US012703718B2

(12) United States Patent
Von Borstel et al.

(10) Patent No.: US 12,703,718 B2
(45) Date of Patent: Aug. 11, 2026

(54) COMPOSITIONS AND COMPOUNDS FOR CO-DELIVERY OF URIDINE AND KETOLEUCINE

(71) Applicant: PHARMA CINQ, LLC, Rockville, MD (US)

(72) Inventors: Reid Warren Von Borstel, Potomac, MD (US); David Michael Simpson, North Bethesda, MD (US); Rolando Alejandro Garcia Garcia, Germantown, MD (US)

(73) Assignee: PHARMA CINQ, LLC, Rockville, MD (US)

( * ) Notice: Subject to any disclaimer, the term of this patent is extended or adjusted under 35 U.S.C. 154(b) by 427 days.

(21) Appl. No.: 18/547,053

(22) PCT Filed: Feb. 2, 2022

(86) PCT No.: PCT/US2022/014874
§ 371 (c)(1),
(2) Date: Aug. 18, 2023

(87) PCT Pub. No.: WO2022/177740
PCT Pub. Date: Aug. 25, 2022

(65) Prior Publication Data

US 2024/0158431 A1 May 16, 2024

Related U.S. Application Data

(60) Provisional application No. 63/228,304, filed on Aug. 2, 2021, provisional application No. 63/151,849, filed on Feb. 22, 2021, provisional application No. 63/151,750, filed on Feb. 21, 2021.

(51) Int. Cl.
*C07H 19/067* (2006.01)
*A61K 31/7072* (2006.01)

(52) U.S. Cl.
CPC ....... *C07H 19/067* (2013.01); *A61K 31/7072* (2013.01)

(58) Field of Classification Search
CPC .......................... C07H 19/067; A61K 31/7072
USPC ......................................... 514/50; 536/28.53
See application file for complete search history.

(56) References Cited

U.S. PATENT DOCUMENTS

| | | | | |
|---|---|---|---|---|
| 5,585,512 | A | 12/1996 | Yamazaki et al. | |
| 7,709,459 | B2 * | 5/2010 | von Borstel | A61P 3/00 514/49 |
| 7,915,233 | B1 | 3/2011 | Von Borstel | |
| 9,566,257 | B2 | 2/2017 | Jalan et al. | |
| 2001/0025032 | A1 | 9/2001 | Von Borstel et al. | |
| 2004/0102523 | A1 | 5/2004 | Broquaire et al. | |
| 2012/0259016 | A1 | 10/2012 | Jalan et al. | |
| 2014/0142186 | A1 | 5/2014 | Scharschmidt et al. | |
| 2018/0318381 | A1 | 11/2018 | Vockley et al. | |
| 2023/0357304 | A1 | 11/2023 | Von Borstel et al. | |
| 2023/0416292 | A1 | 12/2023 | Garcia Garcia et al. | |

FOREIGN PATENT DOCUMENTS

| | | | | |
|---|---|---|---|---|
| CN | 1031536 A | 3/1989 | | |
| EA | 018007 B1 | 4/2013 | | |
| EP | 3335735 A1 | 6/2018 | | |
| JP | H02-32094 A | 2/1990 | | |
| JP | 2002-523434 A | 7/2002 | | |
| JP | 2007-510734 A | 4/2007 | | |
| KR | 10-0818202 B1 | 3/2008 | | |
| RU | 2659388 C1 | 7/2018 | | |
| WO | 2000/050043 A1 | 8/2000 | | |
| WO | WO-2013012760 A1 * | 1/2013 | A61P 9/00 | |
| WO | 2014/160502 A1 | 10/2014 | | |
| WO | 2016/028894 A1 | 2/2016 | | |
| WO | 2019/152776 A1 | 8/2019 | | |
| WO | 2022/056428 A1 | 3/2022 | | |
| WO | 2022/089612 A1 | 5/2022 | | |
| WO | 2022/119784 A1 | 6/2022 | | |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al., "Modern Pharmaceutics, 3ed.", Marcel Dekker, New York, 1996, p. 596. (Year: 1996).*
International Search Report in PCT/US2021/050149, dated Dec. 23, 2021.
International Search Report in PCT/US2021/061053, dated Feb. 7, 2022.
Pubchem, Substance Record for SID 45985391, Available Date: Dec. 5, 2007. <https://pubchem.ncbi.nlm.nih.gov/substance/45985391>.
Pubchem, Substance Record for SID 47237025, Available Date: Jun. 22, 2015. <https://pubchem.ncbi.nlm.nih.gov/substance/47237025>.
Kubasov et al., "Chemical kinetics and catalysis. Part 1," Moscow University Publishing House: 2-3 (2004).
Novosibirsk, "Fundamentals of medical prevention," Educational and Methodical Manual for Students and Cadets of Advanced Training Cycles of State Professional Educational Institutions UDC 614.2-084, BBK 51.1(2)2:13-21 (2016).
Smith et al., "Organic synthesis. Science and Art," Moscow Mir 573:64 (2001).
Non-Final Office Action dated Jul. 14, 2025, in U.S. Appl. No. 18/021,907.
Database PubChem, PubChem CID: 9913736, Available Date: Oct. 25, 2006. <https://pubchem.ncbi.nlm.nih.gov/compound/9913736>.
International Search Report in PCT/US2022/014874, dated May 6, 2022.

(Continued)

*Primary Examiner* — Traviss C McIntosh, III
(74) *Attorney, Agent, or Firm* — MEDLER FERRO WOODHOUSE & MILLS PLLC

(57) ABSTRACT

Compounds and compositions that deliver both uridine and ketoleucine are useful in treating disorders characterized by diminished muscle strength or diminished muscle lean mass. One such a compound is 5'-O-ketoleucyl-2',3'-di-O-acetyluridine.

7 Claims, 2 Drawing Sheets

(56) References Cited

OTHER PUBLICATIONS

McGregor et al., "Alkaline Bromine Oxidation of Amino Acids and Peptides: Formation of a-Ketoacyl Peptides and Their Cleavage by Hydrogen Peroxide," Biochemistry 1(1):53-60 (1962).
Ashour et al., "5-(m-Benzyloxybenzyl)barbituric acid acyclonucleoside, a uridine phosphorylase inhibitor, and 2',3',5'-tri-O-acetyluridine, a prodrug of uridine, as modulators of plasma uridine concentration. Implications for chemotherapy," Biochemical Pharmacology, 51(12):1601-1611 (1996).
Caldovic et al., "Genotype-Phenotype Correlations in Ornithine Transcarbamylase Deficiency: A Mutation Update," Journal of Genetics and Genomics 42:181-194 (2015).
Latvijas PSR Zinatnu akademijas vestis, Kimijas serija: 745-746 (1977).
Livingston et al., "Body surface area prediction in normal-weight and obese patients", American Journal of Physiology—Endocrinology and Metabolism 281:E586-E591 (2001).
Mosley et al., "Mutant Clone of Chinese Hamster Ovary Cells Lacking 3-Hydroxy-3-methylglutaryl Coenzyme A Reductase," The Journal of Biological Chemistry 258(22):13875-13881 (1983).
Non-Final Office Action dated Sep. 22, 2025, in U.S. Appl. No. 18/036,744.
Notice of Allowance dated Nov. 13, 2025, in U.S. Appl. No. 18/021,907.
Notice of Allowance dated Jan. 22, 2026, in U.S. Appl. No. 18/036,744.
Zheng et al., "Production of N-acetylglucosamine by Biosynthesis," Beijing University of Chemical Technology: A Master's Thesis (2019).

* cited by examiner

COMPOSITIONS AND COMPOUNDS FOR CO-DELIVERY OF URIDINE AND KETOLEUCINE

BACKGROUND

Age-related neuromuscular dysfunction underlies several major disease conditions, including sarcopenia and muscle disuse atrophy. Both of these conditions involve impairment of energy metabolism in muscle and in the nervous system, as well as loss of muscle mass. A satisfactory treatment for these conditions should address both pathogenic factors, defective energy metabolism and loss of muscle protein.

Oral delivery of uridine for therapeutic purposes is limited by its poor bioavailability, approximately 7% in both humans and mice. Ester prodrugs of uridine have been found to improve its bioavailability, though only one, 2',3',5,-tri-O-acetyluridine (or uridine triacetate) has been found adequate to deliver sufficient uridine for some clinical purposes. The bioavailability of oral uridine triacetate has been measured at approximately 50% (Ashour 1996).

SUMMARY OF THE INVENTION

This invention provides the compound 5'-O-ketoleucyl-2',3'-di-O-acetyluridine, which is also known as 2',3'-di-O-acetyl-5'-O-(α-ketoisocaproyl)uridine. It also provides a composition comprising a therapeutically effective amount of a combination of a ketoleucine compound and a uridine prodrug.

This invention provides compositions, compounds and methods for treating or preventing sarcopenia (and other muscle-wasting conditions such as cachexia), dynapenia (pathologically diminished muscle strength), exercise intolerance (pathologically diminished endurance during exertion) and muscle disuse atrophy. Also encompassed are conditions associated with a high risk of muscle wasting and exercise intolerance, including chronic kidney disease, chronic obstructive pulmonary disease (COPD) and chronic heart failure. Specifically, compositions and compounds are provided that deliver therapeutic amounts of both uridine and ketoleucine.

Group-1: 4% UTA Diet, NaCl drinking water

Group-2: 4% UTA diet, NaKL drinking water

Group-3: Chow diet, regular drinking water, UTA/NaCl gavage

Group-4: Chow diet, regular drinking water, UTA/NaKL gavage

Group-5: Chow diet, NaKL drinking water, UTA gavage

Figure 1:
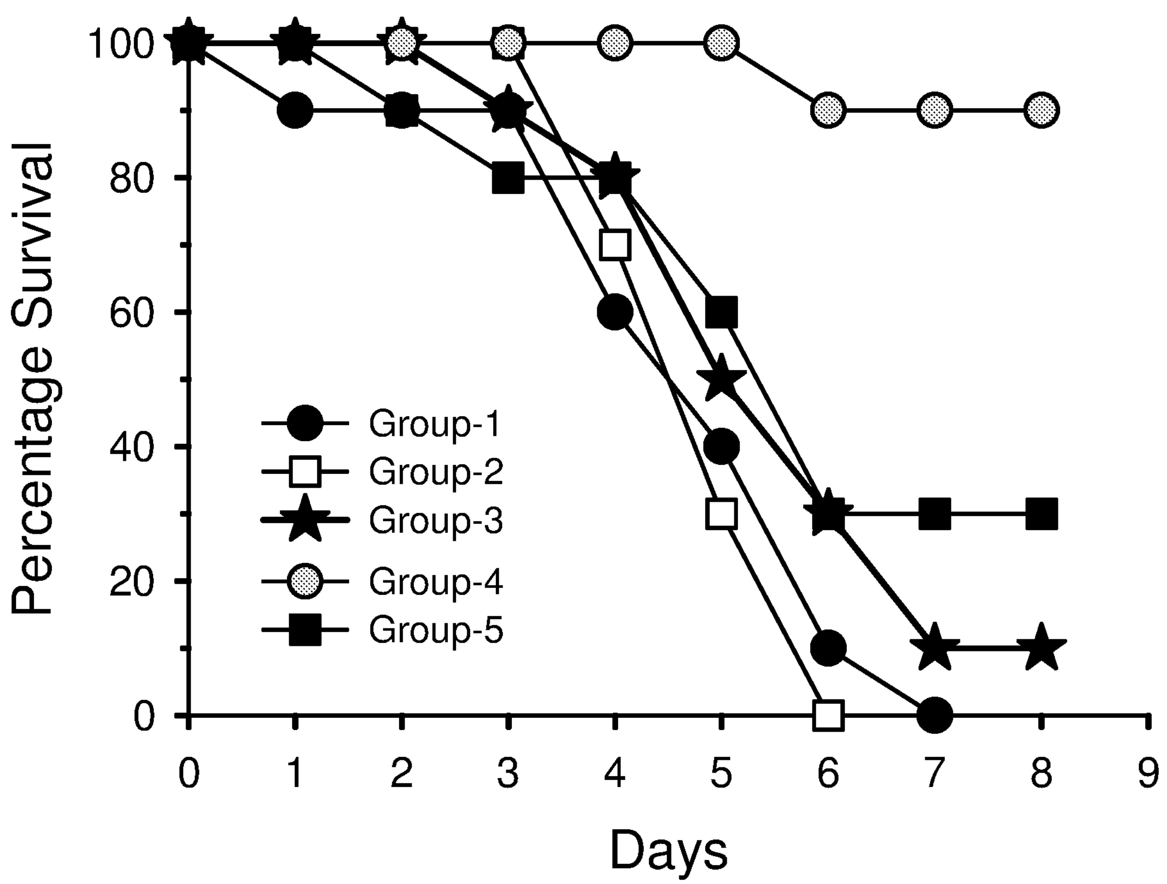
FIG. 1: Survival in Mice Treated With 3-NP, UTA and NaKL
Figure 2:
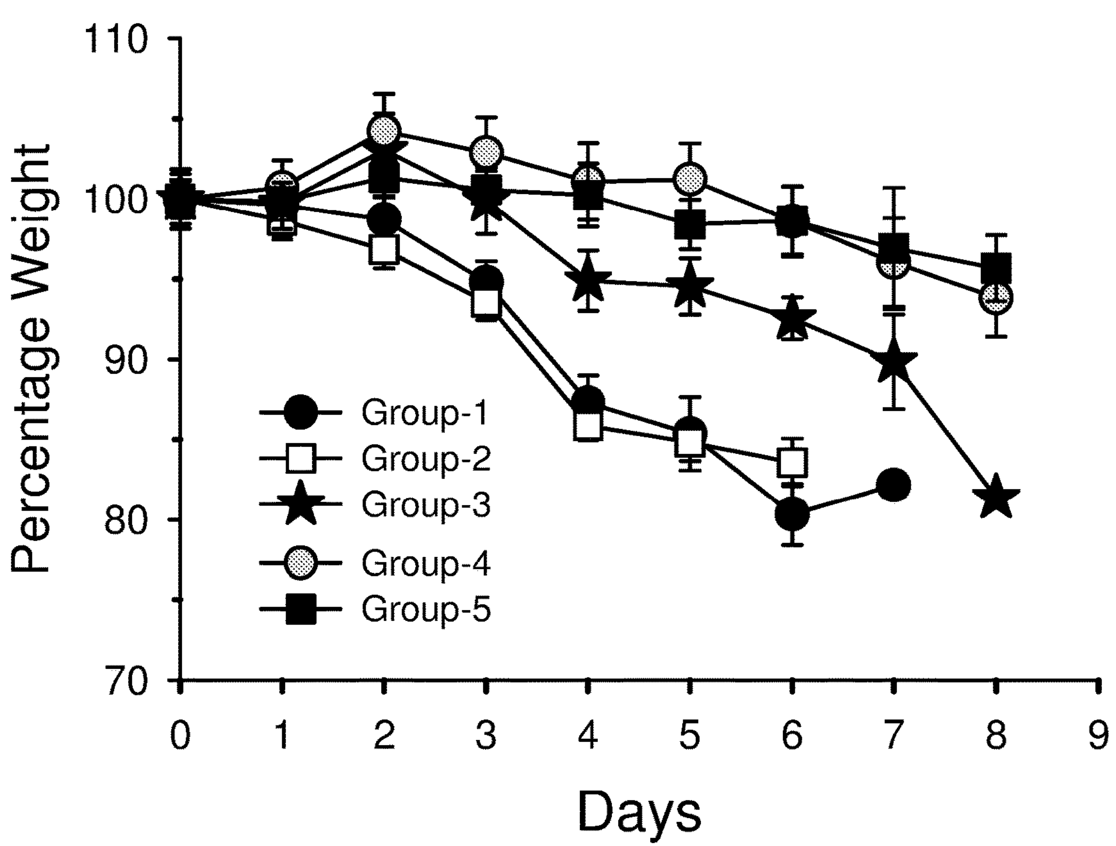

FIG. 2: Percentage Weight Loss in Mice Treated With 3-NP, UTA and NaKL

Group-1: 4% UTA Diet, NaCl drinking water

Group-2: 4% UTA diet, NaKL drinking water

Group-3: Chow diet, regular drinking water, UTA/NaCl gavage

Group-4: Chow diet, regular drinking water, UTA/NaKL gavage

Group-5: Chow diet, NaKL drinking water, UTA gavage

DETAILED DESCRIPTION OF THE INVENTION

Ketoleucine (alpha-ketoisocaproic acid; 4-methyl-2-oxovalerate; KL) is a deaminated derivative of the essential branched-chain amino acid leucine. Leucine is not only a constituent of proteins including those in skeletal muscle, but also acts as a regulator of muscle protein maintenance. Leucine metabolites including ketoleucine and β-hydroxy-β-methylbutyrate can activate or maintain muscle protein synthesis.

Ketoleucine is also a pathogenic factor in certain metabolic disorders. Maple Syrup Urine Disease (MSUD; so-called because of the characteristic odor of urine, resembling that of maple syrup) is a rare genetic disorder caused by a deficiency of an enzyme complex, branched-chain alpha-keto acid dehydrogenase. This results in an impairment of catabolism of branched chain amino acids and their deamination products, causing them to accumulate in brain and other tissues, and accounting for the odor of urine and other bodily fluids. MSUD features progressive neurological dysfunction starting with lethargy, irritability and poor feeding, and followed by neurological signs such as abnormal movements, increasing spasticity, and ultimately, by seizures and deepening coma. If untreated, progressive brain damage is inevitable and death occurs usually within weeks or months. Ketoleucine accumulation impairs cerebral energy metabolism, in part by inhibiting creatine kinase, a crucial enzyme for relay of energy derived from mitochondrial ATP to cytosolic sites of energy usage.

It is therefore unexpected that a combination of oral ketoleucine with oral uridine triacetate provided protection against mortality in a model of severe mitochondrial energy failure greater than that imparted by uridine triacetate or ketoleucine alone.

Ketoleucine is also a short-chain ketoacid. The disclosure also encompasses prodrugs of uridine comprising ketoleucine as a 5'-ester substituent, with optional 2' and/or 3' substituents comprising acetate or other carboxylic acids with 2 or 3 carbon atoms. A ketoleucine substituent in the 5' position of the ribose moiety, combined with acetate substituents in the 2' and 3' positions yields a novel compound that delivers uridine into the circulation, while also delivering a prodrug substituent that provides additional or complementary therapeutic benefit, beyond facilitating uridine delivery.

The primary clinical indications for either prodrugs of uridine with a ketoleucine substituent or combinations of uridine triacetate plus ketoleucine are for prevention and treatment of skeletal muscle wasting disorders, including but not limited to muscle disuse atrophy (e.g. loss of muscle mass and strength caused by immobilization and lack of exercise during prolonged hospitalization) and sarcopenia (loss of lean muscle mass) or dynopenia (loss of muscle strength, with or without loss of muscle mass). A higher risk and incidence of sarcopenia and dynopenia is found in people with comorbidities including chronic kidney disease, COPD and chronic heart failure, and compounds and compositions of this disclosure are suitable for treatment and prevention of these conditions. Cancer-related cachexia, pathologic loss of weight and muscle mass, is also treatable or preventable with agents of this disclosure.

Appropriate doses of compounds and compositions of this invention deliver to human subjects the equivalent of 1 to 5 grams of uridine per dose, advantageously 2-4 grams per dose, given orally 1 to 3 times per day. In a combination of uridine triacetate plus ketoleucine (generally in the form of sodium ketoleucine or other salts), the ketoleucine is present in the combination drug product at a molar equivalent ranging from 1 to a maximum of 4 times the molar amount of uridine. The molecular weight of ketoleucine is approximately 130 Daltons, compared to 370 for uridine triacetate.

Example 1: Synthesis of 2',3'-di-O-acetyl-5'-O-(α-ketoisocaproyl)uridine

Preparation of 5'-O-(tert-butyldimethylsilyl)uridine

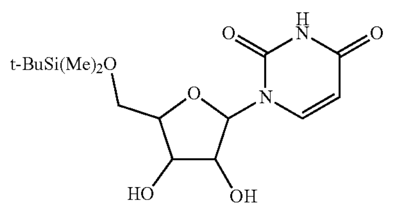

Imidazole (32.68 g, 480 mmoles) and tert-butyl(chloro) dimethylsilane (36.2 g, 240 mmoles) were added sequentially to a solution of uridine (48.84 g, 200 mmoles) in DMF (300 mL) cooled to 0° C. The mixture was stirred at 0° C. for 4 hrs. and at room temperature for 17 hrs. TLC (silica gel, 10% MeOH/DCM) showed the completion of the reaction. DMF was removed using a rotary evaporator under high vacuum. The crude product was dissolved in ethyl acetate and washed with water (3×500 mL). The organic layer was dried with anhydrous $MgSO_4$ and concentrated to give an 88% yield of the monosilylated uridine as a crystalline compound with traces of silyl impurities, as confirmed by $^1H$ NMR (400 MHz, $CDCl_3$) δ 0.11 (s, 6H), 0.92 (s, 9H), 3.84 (dd, 1H, J=1.8, 11.7 Hz), 4.02 (dd, 1H, J=2.2, 11.7 Hz), 4.10-4.30 (m, 3H), 5.68 (d, 1H, J=8.1 Hz), 5.88 (d, 1H, J=2.2 Hz), 8.07 (d, 1H, J=8.0 Hz).

Preparation of 5'-O-(tert-butyldimethylsilyl)-2',3'-di-O-acetyluridine

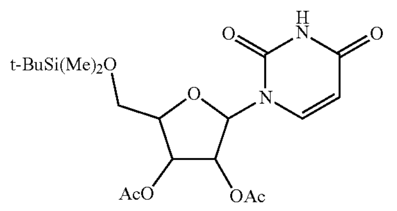

5'-O-(tert-Butyldimethylsilyl)uridine (52.0 g, 145 mmoles) was dissolved in DCM (700 mL), and DMAP (40 g, 328 mmoles) and acetic anhydride (35 mL, 371 mmoles) were added sequentially. The reaction mixture was stirred at room temperature for 4 hrs. under argon. TLC (silica gel, 50% ethyl acetate/hexane) showed the completion of the reaction. The reaction mixture was transferred into a separatory funnel and washed with water (2×500 mL). The organic layer was dried with anhydrous $MgSO_4$, concentrated, and purified using flash chromatography (silica gel, 50% ethyl acetate/hexane) to yield 66.0 g (100%) of product. $^1H$ NMR (400 MHz, $CDCl_3$) δ 0.11 (s, 6H), 0.92 (s, 9H), 2.05 (s, 3H), 2.11 (s, 3H), 3.81 (m, 1H), 3.90 (m, 1H), 4.19-4.20 (m, 1H), 5.27-5.33 (m, 2H), 5.72 (dd, 1H, J=1.8, 8.0 Hz), 6.28 (d, 1H, J=6.6 Hz), 7.84 (d, 1H, J=8.1 Hz), 8.78 (s, 1H); $^{13}C$ NMR (100 MHz, $CDCl_3$) δ −5.48, −5.45, 18.45, 20.54, 20.83, 25.99, 63.34, 71.88, 73.52, 83.94, 85.47, 103.41, 139.64, 150.88, 163.24, 169.77, 170.07.

Preparation of 2',3'-di-O-acetyluridine

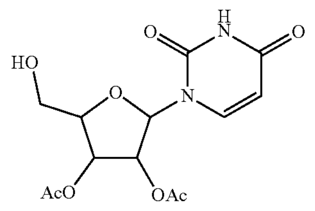 [SMILES: CC(=O)OC1C(CO)OC(n2ccc(=O)[nH]c2=O)C1OC(C)=O]

Four grams of para-toluenesulfonic acid were added to a solution of 5'-O-(tert-butyldimethylsilyl)-2',3'-di-O-acetyluridine (66.0 g, 0.149 mole) in dry MeOH (100 mL) and dry DCM (250 mL) cooled to 0° C. The reaction mixture was stirred at 0° C. for 3 hrs. and then at room temperature overnight. TLC (silica gel, 50% ethyl acetate/hexane showed the consumption of the starting material. The reaction mixture was quenched with triethylamine and evaporated to dryness. The crude product was chromatographed using silica gel and hexane/ethyl acetate (1:1) to yield: 39.5 g (81%) of the product. $^1H$ NMR (400 MHz, $CDCl_3$) δ 2.08 (s, 3H), 2.13 (s, 3H), 2.73 (s, 1H), 3.85 (dd, 1H, J=2.2, 12.1 Hz), 3.94 (dd, 1H, J=2.2, 12.1 Hz), 4.21 (q, 1H, J=2.2 Hz), 5.45-5.49 (AB, 2H), 5.78 (dd, 1H, J=1.9, 8.1 Hz), 6.06 (m, 1H), 7.75 (d, 1H, J=8.1 Hz), 8.90 (s, 1H); $^{13}C$ NMR (100 MHz, $CDCl_3$) δ 20.64, 20.85, 62.03, 71.41, 73.19, 83.69, 87.86, 103.45, 140.93, 150.71, 163.28, 169.97, 170.28.

Preparation of 2',3'-di-O-acetyl-5'-O-(α-ketoisocaproyl)uridine

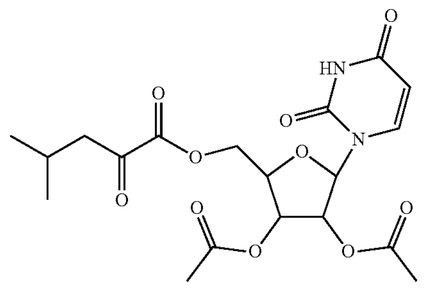 [SMILES: CC(=O)OC1C(COC(=O)C(=O)CC(C)C)OC(n2ccc(=O)[nH]c2=O)C1OC(C)=O]

Dichloromethyl methyl ether (5.00 mL, 56.5 mmol) was added dropwise to α-ketoisocaproic acid (5.0 g, 38.5 mmol), during which gaseous HCl is evolved. After the addition is completed, the mixture is heated at 48-52° C. for 30 minutes. Then, the mixture is cooled quickly with an ice bath. The mixture is added slowly via syringe to a mixture of 2',3'-di-O-acetyluridine (12.6 g, 38.4 mmol) and pyridine (9.0 mL, 112 mmol) in 180 mL of DCM cooled by an ice bath. The mixture was allowed to warm to room temperature overnight. Five mL of water were added, and the solvent was evaporated. The residue was partitioned between ethyl acetate (3×250 mL) and 1M HCl (2×200 mL), 0.1M HCl (100 mL), and brine (200 mL). The combined organic phases were dried over anhydrous $MgSO_4$, and the solvent was evaporated. Purification by flash chromatography (60% ethyl acetate/hexanes) gave 14.2 g of the product as a white foamy solid (84%). $^1H$ NMR (400 MHz, $CDCl_3$) δ 0.97-0.99 (m, 6H), 2.10 (s, 3H), 2.14 (s, 3H), 2.18-2.24 (m, 1H), 2.72-2.85 (m, 2H), 4.37-4.41 (m, 2H), 4.48-4.55 (m, 1H), 5.35-5.40 (m, 2H), 5.86 (dd, 1H, J=2, 8 Hz), 6.25 (d, 1H, J=6 Hz), 7.77 (d, 1H, J=8 Hz), 9.14 (br s, 1H); $^{13}C$ NMR (100 MHz, $CDCl_3$) δ 20.35, 20.51, 22.35, 22.39, 24.14, 47.45, 64.59, 70.66, 72.35, 79.87, 86.30, 103.74, 139.88, 150.51, 160.02, 162.77, 169.43, 169.73, 193.08.

Example 2: Protective Effects of Oral Uridine Triacetate and Ketoleucine in a Mouse Model of Mitochondrial Dysfunction A combination of uridine triacetate and ketoleucine was assessed in a model of progressive and lethal impairment of mitochondrial oxidative phosphorylation. 3-nitropropionic acid (3-NP), an irreversible inhibitor of Complex II of the mitochondrial electron transport chain. Daily administration of 3-NP results in progressive loss of mitochondrial reserve energy capacity, until the threshold for baseline energy requirements for survival is breached, resulting in mortality from both heart failure and central nervous system dysfunction.

In this study, uridine triacetate was administered as either by gavage as an oral bolus, or by incorporation into rodent chow at a concentration of 4% w/w. Similarly, ketoleucine (in the form of its sodium salt; NaKL) was administered in different groups by gavage or by dissolving it in drinking water. Sodium chloride (NaCl) was used as a control substance in some groups to account for the sodium load from the ketoleucine salt.

Chemical(s): Hydroxypropyl methyl cellulose (HPMC), cat #H3785, Lot #SLBS5701, CAS 9004-65-3, SIGMA-Aldrich. Uridine Triacetate for gavage (UTA), item, D000156, Lot #Q000001095, Almac Sciences, Uridine Triacetate in the diet (UTA), item & Lot #, D000302, 2148-070, Project #1314A0071A, recovery of material from R-104 Lot Q000003578, Almac Sciences, Sodium Chloride (NaCl), VWR, Cat #BDH9286-500G, Lot #1976C500, CAS 7647-14-5, 4-methyl-2-oxovaleric acid sodium salt (ketoLeucine: NaKL), cat #M326425, Lot #1-AWT-36-1, CAS4502-00-5, Toronto Research Chemicals, and 3-nitropropionic acid (3NP), cat #N5636, Lot #11101616, CAS 504-88-1, SIGMA-Aldrich.

Vehicle(s): UTA, NaKL, or NaCl in suspensions was prepared in 0.75% HPMC. NaCL or NaKL in the drinking water were prepared by dissolving in water. 3-NP solutions were prepared in water.

Dosing Formulation(s): Preparation: UTA was suspended in 0.75% HPMC at 50 mg/ml. NaKL will be suspended in 0.75% HPMC at 100 mg/ml, or included in the drinking water at 15.8 mg/ml. The groups not receiving NaKL received an amount of NaCL by gavage (38.4 mg/ml) or in the drinking water (6.1 mg/ml) which are equimolar with the sodium contributed by NaKL. NaKL in the drinking water was filter sterilized after preparation. Drinking water with NaKL was changed every 4 days.

3NP was weighed and dissolved in water, neutralized with 1 N NaOH to pH 7, and filtered sterile. Final concentration will be 6.5 mg/ml.

Dosing: Some groups of mice were gavaged with a UTA suspension containing 50 mg/ml UTA (0.02 ml/g bw, dose: 1,000 mg/Kg) or with a similar UTA suspension also containing 100 mg/ml NaKL (0.02 ml/g bw, dose: 2,000 mg/Kg), or 38.42 mg/ml NaCl (0.02 ml/g bw, dose: 768 mg/Kg). Some mice will have NaKL (15.6 mg/ml, 104 mM) or an equimolar amount of NaCL (6.1 mg/ml) in the drinking water Mice were injected ip (0.01 ml/g bw) with 6.5 mg/ml 3-NP for a dose of 65 mg/Kg.

Animals: Female CD-1 mice.

| Species | Strain | Gender | Number | Age and Weight Range at Shipment | Vendor | Diet and Housing |
|---|---|---|---|---|---|---|
| Mouse | CD-1 | Males Females | 50 | DOB: Feb. 22, 2019 | Envigo | Harlan Teklad 2016, ad libitum, housed 5/cage |

General Experimental

Design: For the experiment 50 mice were divided into 5 groups of 10 animals each: Group-1, Group-2, Group-3, Group-4, and Group-5.

Group-1 was fed a diet of 4% UTA and had access to water containing an amount of NaCl equimolar to that contributed by NaKL in the drinking water of other groups (104 mM, 6.1 mg NaCl/ml). The mice were injected intraperitoneally with 6.5 mg/ml 3-NP (0.01 ml/g bw) at 5 PM.

Group-2 will be fed a diet of 4% UTA and had access to water containing NaKL at 15.6 mg NaKL/ml; 104 mM). The mice were injected intraperitoneally with 6.5 mg/ml 3-NP (0.01 ml/g bw) at 5 PM.

Group-3 were gavaged with 1000 mg/Kg UTA and 768 mg/Kg NaCl at 7 AM, and 4 PM, The mice were injected intraperitoneally with 6.5 mg/ml 3-NP (0.01 ml/g bw) at 5 PM.

Group-4 was gavaged with 1000 mg/Kg UTA+2000 mg/Kg NaKL at 7 AM, and 4 PM, and injected intraperitoneally with 6.5 mg/ml 3-NP (0.01 ml/g bw) at 5 PM.

Group-5 was gavaged with 1000 mg/Kg UTA at 7 AM and 4 PM, and had access to water containing 15.6 mg/ml NaKL. The mice were injected intraperitoneally with 6.5 mg/ml 3-NP (0.01 ml/g bw) at 5 PM.

The mice in groups 1 and 2 were started on the 4% UTA diet on Monday 5-6-19. Mice in groups 1, 2, and 5 were started on their respective drinking water treatments on Monday 5-6-19 too. This was to avoid the chance that the mice will associate any side effects of 3NP injection with changes in the drinking water or the diet and thereby cause aversion to necessary nutrition and fluid intake. Mice 3, 4, and 5 commenced 7 AM and 4 PM gavage treatments on Wednesday 5-8-19. All mice commenced 5 PM 3NP treatments on Wednesday 5-8-19.

Body weights were evaluated when structuring the groups on Monday 5-6 before placing the mice on diets and drinking water treatments. Weight was again evaluated again on Tuesday 5-7. Weight loss and mortality were evaluated in the morning daily beginning on Wednesday 5-8 before commencing the treatments, and treatments were planned to continue for at least 14 days, depending on onset and extent of mortality.

TABLE 1

| Summary of Groups and Treatments | | | | | |
|---|---|---|---|---|---|
| Group | Diet | Water | 7:00 AM | 4:00 PM | 5:00 PM |
| 1 | 4% UTA | NaCl in Water | — | — | 3-NP (65 mg/Kg) |
| 2 | 4% UTA | NaKL in Water | — | — | 3-NP (65 mg/Kg) |
| 3 | Normal Chow | Regular Water | UTA (1000 mg/Kg and NaCl by gavage) | UTA (1000 mg/Kg and NaCl by gavage) | 3-NP (65 mg/Kg) |
| 4 | Normal Chow | Regular Water | UTA/NaKL (1000 mg/Kg UTA & 2000 mg/Kg NaKL by gavage) | UTA/NaKL (1000 mg/Kg UTA & 2000 mg/Kg NaKL by gavage) | 3-NP (65 mg/Kg) |
| 5 | Normal Chow | NaKL in Water | UTA (1000 mg/Kg by gavage) | UTA (1000 mg/Kg by gavage) | 3-NP (65 mg/Kg) |

The combination of uridine triacetate and NaKL with both agents given by gavage was strikingly more effective in prevent mortality than either agent alone given by gavage or in chow, and was also more effective than when both uridine triacetate and NaKL were administered together in chow and drinking water respectively. This is likely due to greater efficacy of higher peak concentrations of plasma uridine and ketoleucine obtained after oral bolus dosing versus the smaller but more prolonged elevation of systemic uridine and NaKL (and its metabolites) after administration in chow or drinking water. Uridine triacetate given by oral gavage and NaKL in drinking water (Group 5) was more effective against mortality than the other groups, apart from oral gavage bolus administration of uridine triacetate and NaKL (Group 3).

Bolus (gavage) uridine triacetate with or without NaKL (Groups 3-5) provided better protection against weight loss than did 4% (w/w) uridine triacetate in rodent chow (Groups 1 and 2), despite a larger total uridine triacetate dose per day in animals receiving it in their chow (~8000 mg/kg/day). Bolus UTA yields higher peak plasma uridine concentrations than does UTA in chow, indicating that the protective mechanism is better activated by periodic high peak uridine versus constant lower-level systemic exposure.

TABLE 2

| Survival Results | | | | |
|---|---|---|---|---|
| Group | Diet | Water | Gavage | Survival at d 8 |
| 1 | 4% UTA | NaCl in Water | — | 0/10 |
| 2 | 4% UTA | NaKL in Water | — | 0/10 |
| 3 | Normal Chow | Regular Water | UTA (1000 mg/Kg and NaCl by gavage) | 1/10 |
| 4 | Normal Chow | Regular Water | UTA/NaKL (1000 mg/Kg UTA & 2000 mg/Kg NaKL by gavage) | 9/10 |
| 5 | Normal Chow | NaKL in Water | UTA (1000 mg/Kg by gavage) | 3/10 |

What is claimed is:

1. A compound, 5'-O-ketoleucyl-2',3'-di-O-acetyluridine.

2. A method of treating a disorder characterized by diminished muscle strength or diminished muscle lean mass in a mammalian subject, comprising administering to the mammalian subject an amount of the compound of claim 1 effective to treat the disorder.

3. The method of claim 2, wherein the disorder is selected from the group consisting of muscle-wasting conditions; dynapenia; muscle disuse atrophy; and the muscle wasting and exercise tolerance associated with chronic kidney disease, chronic obstructive pulmonary disease, and chronic heart failure.

4. The method of claim 3 wherein the muscle-wasting condition is selected from the group consisting of sarcopenia and cachexia.

5. The method of claim 2, wherein the mammalian subject is a human subject.

6. The method of claim 3, wherein the mammalian subject is a human subject.

7. The method of claim 4, wherein the mammalian subject is a human subject.

* * * * *